(12) United States Patent
Regberg et al.

(10) Patent No.: US 10,724,108 B2
(45) Date of Patent: Jul. 28, 2020

(54) METHODS FOR ISOLATING NUCLEIC ACIDS FROM SAMPLES

(71) Applicant: ExxonMobil Upstream Research Company, Spring, TX (US)

(72) Inventors: Aaron B. Regberg, Houston, TX (US); Zarath M. Summers, High Bridge, NJ (US); A. Lucie N'Guessan, Houston, TX (US); John B. Kirkpatrick, Narragansett, RI (US); Steven L. D'Hondt, Narragansett, RI (US)

(73) Assignee: ExxonMobil Upstream Research Company, Spring, TX (US)

( * ) Notice: Subject to any disclaimer, the term of this patent is extended or adjusted under 35 U.S.C. 154(b) by 389 days.

(21) Appl. No.: 15/600,161

(22) Filed: May 19, 2017

(65) Prior Publication Data

US 2017/0342467 A1 Nov. 30, 2017

Related U.S. Application Data

(60) Provisional application No. 62/343,463, filed on May 31, 2016.

(51) Int. Cl.
| | | |
|---|---|---|
| *C12Q 1/68* | (2018.01) | |
| *C07H 21/00* | (2006.01) | |
| *C12Q 1/689* | (2018.01) | |
| *C12N 15/10* | (2006.01) | |
| *G01N 1/30* | (2006.01) | |
| *G01N 1/40* | (2006.01) | |
| *G01N 1/42* | (2006.01) | |
| *B01D 11/04* | (2006.01) | |
| *C12Q 1/6806* | (2018.01) | |
| *C12Q 1/6848* | (2018.01) | |

(52) U.S. Cl.
CPC .......... *C12Q 1/689* (2013.01); *B01D 11/0492* (2013.01); *C12N 15/1003* (2013.01); *C12N 15/1017* (2013.01); *C12Q 1/6806* (2013.01); *G01N 1/30* (2013.01); *G01N 1/4077* (2013.01); *G01N 1/42* (2013.01); *C12Q 1/6848* (2013.01); *C12Q 2600/158* (2013.01)

(58) Field of Classification Search
CPC ...... C12N 15/1003; C12Q 1/68; C07H 21/00; C12P 19/34
See application file for complete search history.

(56) References Cited

U.S. PATENT DOCUMENTS

| | | | | |
|---|---|---|---|---|
| 3,845,941 A | * | 11/1974 | Mendenhall | ........ E01C 19/1036 366/24 |
| 4,056,969 A | * | 11/1977 | Barringer | ................. G01V 5/02 250/255 |
| 4,485,071 A | * | 11/1984 | Larter | ..................... G01N 25/14 422/78 |
| 4,633,182 A | * | 12/1986 | Dzwinel | .................. G01V 3/12 324/335 |
| 5,318,116 A | * | 6/1994 | Vinegar | .................. B09C 1/005 166/60 |
| 5,922,536 A | * | 7/1999 | Nivens | ................. C12O 1/6806 435/134 |
| 6,613,520 B2 | | 9/2003 | Ashby | |
| 7,297,661 B2 | | 11/2007 | Beyer et al. | |
| 7,571,644 B2 | | 8/2009 | Ibrahim et al. | |
| 7,762,131 B2 | | 7/2010 | Ibrahim et al. | |
| 8,071,285 B1 | | 12/2011 | Lawyer et al. | |
| 8,071,295 B2 | | 12/2011 | Ashby | |
| 8,120,362 B2 | | 2/2012 | Combee | |
| 8,355,872 B2 | | 1/2013 | Russell et al. | |
| 8,361,725 B2 | | 1/2013 | Russell et al. | |
| 8,476,011 B1 | | 7/2013 | Short | |
| 8,476,016 B2 | | 7/2013 | Ashby | |
| 8,883,417 B2 | | 11/2014 | Jacobs et al. | |
| RE45,349 E | | 1/2015 | Short | |
| 8,950,251 B2 | | 2/2015 | Valentine | |
| 9,146,225 B2 | | 9/2015 | Pottorf et al. | |
| 9,206,680 B2 | | 12/2015 | Ashby et al. | |
| 9,593,160 B2 | | 3/2017 | Ingber et al. | |
| 9,593,382 B2 | | 3/2017 | Kunin et al. | |
| 9,612,231 B2 | | 4/2017 | Pottorf et al. | |
| 9,670,395 B2 | | 6/2017 | McDaniel | |
| 2001/0010910 A1 | * | 8/2001 | Hyldig-Nielsen | ... C07K 14/003 435/6.12 |
| 2002/0016302 A1 | * | 2/2002 | Grynkiewicz | ....... A61K 9/1272 514/34 |
| 2002/0081593 A1 | * | 6/2002 | Nagashima | .......... C12O 1/6888 435/6.12 |

(Continued)

FOREIGN PATENT DOCUMENTS

| | | |
|---|---|---|
| CN | 102154453 A | 8/2011 |
| CN | 102732504 A | 10/2012 |

(Continued)

OTHER PUBLICATIONS

DeLong, E.F., Archaea in costal marine environments. PNAS, USA 89 : 5685 (Year: 1992).*
Rueter et al., Nature 372 :455 (Year: 1994).*
Rabus et al., Degradative Capacities and 16S rRNA-Targeted Whole-Cell Hybridization of Sulfate-Reducing Bacteria in an Anaerobic Enrichment Culture Utilizing Alkylbenzenes from Crude Oil. Applied and Environmental Microbiology 62(10) : 3605-3613 (Year: 1996).*
Magot et al., Microbiology of petroleum reservoirs . Antonie van Leeuwenhoek 77:103 (Year: 2000).*
Yang et al. Chemosphere 43 : 1013 (Year: 2001).*
Hovland et al., Do Norwegian deep-water coral reefs rely on seeping £uids? Marine Geology 198 :83-96 (Year: 2003).*

(Continued)

*Primary Examiner* — Ethan C Whisenant
(74) *Attorney, Agent, or Firm* — ExxonMobil Upstream Research Company—Law Department (57) ABSTRACT

Techniques and methods are provided for isolating nucleic acids from a sample. The methods include adding a chelating agent to the sample to block nucleic acid binding sites on contaminants in the sample; heating the sample to remove hydrocarbons; and lysing the cells using freeze-thaw cycles.

25 Claims, 6 Drawing Sheets

(56) References Cited

U.S. PATENT DOCUMENTS

| | | | |
|---|---|---|---|
| 2002/0086313 A1 | 7/2002 | Kilbane, II et al. | |
| 2002/0102541 A1* | 8/2002 | Wade | C07K 14/47 435/6.11 |
| 2002/0120429 A1 | 8/2002 | Ortoleva | |
| 2002/0164617 A1* | 11/2002 | Felsch | C07K 14/70571 435/6.16 |
| 2003/0098276 A1* | 5/2003 | Carlson | B01D 24/04 210/497.1 |
| 2003/0211494 A1* | 11/2003 | Hreggvidsson | C12N 9/2417 506/10 |
| 2004/0040054 A1* | 2/2004 | Silva | G01N 33/80 435/6.16 |
| 2004/0209249 A1 | 10/2004 | Aevarrson et al. | |
| 2005/0026197 A1* | 2/2005 | Dertinger | G01N 33/80 435/6.16 |
| 2005/0282202 A1* | 12/2005 | Brolaski | C12N 15/1003 435/6.18 |
| 2006/0185034 A1* | 8/2006 | Todd | A01H 5/02 800/282 |
| 2007/0292937 A1* | 12/2007 | Pernthaler | C12N 1/02 435/243 |
| 2008/0040086 A1 | 2/2008 | Betancourt et al. | |
| 2008/0147326 A1 | 6/2008 | Ellis | |
| 2009/0071239 A1 | 3/2009 | Rojas et al. | |
| 2009/0186778 A1 | 7/2009 | Stepanauskas et al. | |
| 2010/0015612 A1 | 1/2010 | Pelham et al. | |
| 2010/0086180 A1 | 4/2010 | Wallace | |
| 2010/0184157 A1* | 7/2010 | Williams | C12N 1/06 435/91.4 |
| 2010/0257004 A1 | 10/2010 | Perlmutter et al. | |
| 2011/0250582 A1 | 10/2011 | Gates et al. | |
| 2011/0308790 A1 | 12/2011 | Strapoc et al. | |
| 2012/0158306 A1 | 6/2012 | Busche et al. | |
| 2012/0165215 A1 | 6/2012 | Anderson et al. | |
| 2012/0244527 A1* | 9/2012 | Trinh | C12O 1/686 435/6.11 |
| 2013/0030712 A1 | 1/2013 | Ashby | |
| 2013/0030714 A1 | 1/2013 | Ashby | |
| 2013/0157275 A1 | 6/2013 | Park et al. | |
| 2013/0164263 A1* | 6/2013 | Kim | A01N 65/00 424/93.5 |
| 2013/0338350 A1* | 12/2013 | Hurt, Jr. | C12N 15/1003 536/25.42 |
| 2014/0011687 A1 | 1/2014 | Ashby | |
| 2014/0011692 A1 | 1/2014 | Ashby | |
| 2014/0147883 A1* | 5/2014 | Prins | G01N 1/2813 435/40.5 |
| 2014/0182840 A1 | 7/2014 | Sheehy et al. | |
| 2014/0200149 A1* | 7/2014 | Andersen | C12O 1/689 506/9 |
| 2014/0256055 A1* | 9/2014 | Pottorf | G01V 9/007 436/163 |
| 2014/0288853 A1 | 9/2014 | Dreyfus et al. | |
| 2014/0303895 A1 | 10/2014 | Dreyfus et al. | |
| 2014/0378319 A1 | 12/2014 | Regberg et al. | |
| 2014/0038348 A1 | 2/2015 | Ashby et al. | |
| 2015/0127313 A1 | 5/2015 | Lawson et al. | |
| 2015/0284810 A1 | 10/2015 | Knight et al. | |
| 2015/0284811 A1 | 10/2015 | Knight et al. | |
| 2015/0291992 A1 | 10/2015 | Al-Moniee et al. | |
| 2015/0354000 A1 | 12/2015 | Borodina et al. | |

FOREIGN PATENT DOCUMENTS

| | | |
|---|---|---|
| CN | 103667255 A | 3/2014 |
| CN | 104630204 A | 5/2015 |
| CN | 104630336 A | 5/2015 |
| CN | 104651350 A | 5/2015 |
| JP | 2009-195179 * | 9/2009 |
| WO | WO 2002/059351 A2 | 8/2002 |
| WO | WO 2004/090164 A2 | 10/2004 |
| WO | WO 2010/109173 A1 | 9/2010 |
| WO | WO 2013/119350 A1 | 8/2013 |
| WO | WO 2013/148442 A1 | 10/2013 |
| WO | WO 2015/103165 A1 | 7/2014 |
| WO | WO 2015/103332 A2 | 7/2015 |

OTHER PUBLICATIONS

LaMontagne et al., Bacterial diversity in marine hydrocarbon seep sediments. Environmental Microbiology 6(8) : 799-808 (Year: 2004).*

Jeanthon et al., Ch. 4. Hyperthermophilic and Methanogenic Archaea in oil fields. in Petroleum Microbiology, ASM, Wahington, D.C. (Year: 2005).*

Maila et al., Soil microbial communities: Influence of geographic location and hydrocarbon pollutants. Soli Biology & Biochemistry (Year: 2006).*

Pham et al., Characterizing microbial diversity in production water from an Alaskan mesothermic petroleum reservoir with two independent molecular methods. Environmental Microbiolgy 11(1) : abstract Only (Year: 2009).*

Wasmund et al., Applied and Environmental Microbiology 75(23) : 7391 (Year: 2009).*

Redmond et al., Identification of Novel Methane-, Ethane-, and Propane-Oxidizing Bacteria at Marine Hydrocarbon Seeps by Stable Isotope Probing. Applied and Environmental Microbiology 76(19) : 6412 (Year: 2010).*

Hawley et al., Metagenomic analysis of microbial consortium from natural crude oil that seeps into the marine ecosystem offshore Southern California. Standards in Genomic Sciences 9: 1259 (Year: 2014).*

Meckenstock et al.,Water droplets in oil are microhabitats for microbial life. Science 345 (6197) : 673 (Year: 2014).*

Ross, Sheldon M. lntroductiuon to Probabilty Models, 11th Ed. Academic Press (Year: 2014).*

Azam et al.,The Ecological Role of Water-Column Microbes in the Sea. Marine Ecology—Progress Series 10: pp. 257-262 (Year: 1983).*

Bauer et al., Microbial biogeochemistry and heterotraphy in sediments of a marine hydrocarbon seep. Limnol.Oceangr., 33 (6, part 2) : pp. 1493-1513. (Year: 1988).*

Kleindienst et al., Diverse, rare microbial taxa responded to the Deepwater Horizon deep-sea hydrocarbon plume. The ISME Journal 10:400-415 (published online Jul. 31, 2015). (Year: 2016).*

Bryant et al. (1989) "Review of Microbial Technology for Improving Oil Recovery", *SPE Reservoir Engineering*, pp. 151-154.

Hohl et al. (2010), "Energy, Environment and Climate Directorate White Paper", DCO Energy, Environment and Climate Workshop, pp. 1-38.

Lazar et al. (2011), "Distribution of Anaerobic Methane-Oxidizing and Sulfate-Reducing Communities in the G11 Nyegga Pockmark Norweigan Sea", *Antoine van Leeuwenhoek*, vol. 100, pp. 639-653.

Li et al. (2014) "Microbial Abudance and Community Composition Influence Production Performance in a Low-Temperature Petroleum Reservoir", *Environmental Science and Technology*, vol. 48, pp. 5336-5344.

Lozano-A et al. (2008) "DNA Extraction from Heavy Oil Contaminated Microcosms and RPOB Gene PCR Amplification", *Actual Biol.*, vol. 30, Issue 88, pp. 7-14.

MacDonald et al. (2002) "Transfer of hydrocarbons from natural seeps to the water column and atmosphere", *Geofluids*, vol. 2, pp. 95-107.

Magoon et al. (1994) "The Petroleum System—From Source to Trap", *AAPG Memoir* 60, pp. 3-24.

Mangelsdorf et al. (2011) "Microbial Lipid Markers Within and Adjacent to Challenger Mound in the Belgica Carbonate Mound Province, Porcupine Basin, Offshore Ireland (IODP Expedition 307)", *Marine Geology*, vol. 282, pp. 91-101.

Nocker A., et al. (2007) "Genotypic Microbial Community Profiling: A Critical Technical Review", Microbiology Ecology, pp. 276-289.

Orphan et al. (2011) "Culutre Depenednet and Culture-Independent Characterization of Microbial Assemblages Assoicated with High- (56) References Cited

OTHER PUBLICATIONS

Temperature Petroleum Reservoirs", *Applied and Environmental Microbiology*, vol. 66, No. 2, pp. 700-711.

Ozgul (2002), "Geochemical Assessment of Gaseous Hydrocarbons: Mixing of Bacterial and Thermogenic Methane in the Deep Subsurface Petroleum System, Gulf of Mexico Continental Slope", Thesis in partial fulfillment of the requirements for the degree of Master of Science at Texas A&M University, pp. 1-167.

Sandrea et al. (2007) "Global Oil Reserves—Recovery Factors Leave Vast Target for EOR Technologies", *Oil & Gas Journal*, pp. 1-8.

Tringe, S.G., et al. (2005) "Comparative Metagenomics of Microbial Communities", Science, vol. 308, pp. 554-557.

Van Hamme et al. (2003) "Recent Advances in Petroleum Microbiology", *Microbiology and Molecular Biology Reviews*, vol. 67, No. 4, pp. 503-549.

Waldron et al. (2007) "Salinity Constraints on Subsurfae and Archael Diversity and Methanogensis in Sedimentary Rock Rich in Organic Matter", *Applied Environmental Microbiology*, vol. 73, No. 13, pp. 4171-4179.

Wang et al. (2015) "Nonequilibirum clumped isotope signals in microbial methane", *Science*, vol. 348, Issue 6233, pp. 428-431.

\* cited by examiner

METHODS FOR ISOLATING NUCLEIC ACIDS FROM SAMPLES

CROSS REFERENCE TO RELATED APPLICATIONS

This application claims the benefit of U.S. Provisional Application No. 62/343,463 filed 31 May 2016, the entirety of which is incorporated herein by reference.

FIELD OF THE INVENTION

Embodiments of the present disclosure relate generally to the field of geochemistry and microbiology. More particularly, the present disclosure relates to methods for extracting and isolating nucleic acids from samples, such as field samples.

BACKGROUND OF THE INVENTION

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

Hydrocarbon reserves are becoming increasingly difficult to locate and access. Typically, various methods are utilized to collect measurement data and then to predict the location of potential hydrocarbon accumulations. For example, reflection seismology is the dominant technique for identifying the location of potential hydrocarbon accumulations. This technique is used to identify structures that may hold hydrocarbon accumulations and may also be utilized to image the hydrocarbon fluids within subsurface accumulations as direct hydrocarbon indicators (DHIs). However, seismic imaging may be challenging in cases where the acoustic impedance contrasts that generate DHIs are great diminished or absent, for example, in the imaging of sub-surface geological features at increasing depth, sub-volcanic features, or sub-salt features. Consequently, seismic imaging technology may lack the required fidelity to provide accurate assessments of the location, volume, and fluid composition of subsurface hydrocarbon accumulations.

Similarly, non-seismic hydrocarbon detection technologies, such as potential field based methods, like gravity or magnetics, may lack the fidelity to identify hydrocarbon accumulations. Other non-seismic hydrocarbon accumulation detection technologies, such as geological extrapolations of structural or stratigraphic trends, may provide exploration prospects, but cannot directly detect hydrocarbon accumulations.

Hydrocarbon seepage at the sea floor or on land may provide some indication of an active or working hydrocarbon system where hydrocarbons have been generated and expulsed. However, hydrocarbons may also be produced from microbial degradation of organic matter in the subsurface that may or may not be associated with an accumulation or reservoir. Thus, it can be difficult to determine whether such hydrocarbon seepages migrated directly from a source rock, from a failed trap without significant residence time within an accumulation, or from an existing hydrocarbon accumulation.

Sequencing of nucleic acids found in field samples may provide information that can be helpful for determining the general source of hydrocarbons in seeps. For example, microorganisms present may be associated with the consumption of subsurface biologic material, forming hydrocarbons, or with the consumption of hydrocarbons released from a reservoir as an energy source. The identification of the microorganisms present may be performed by an analysis of the nucleic acids present in the sample. However, nucleic acids can be difficult to isolate and extract from field samples, such as subsea samples and/or samples containing hydrocarbons.

As a result, there remains a need for enhanced techniques for the isolation and extraction of nucleic acids from field samples. Such enhanced techniques may allow for more effective sequencing of the nucleic acids from, for example, microorganisms, and thus, a more effective determination of the type of hydrocarbons present in a seep.

Background references may include PCT Publication Nos. WO 2010/109173 A1, WO 2013/119350 A1, WO 2015/103165 A1, and WO 2015/103332 A2; US Patent Application Publication Nos. US 2006/0154306 A1, US 2010/0279290 A1, US 2014/0051847 A1, and US 2015/0185126 A1; U.S. Pat. Nos. 6,852,495 B2, 7,459,548 B2, 8,877,918 B2, 9,145,553 B2, 9,416,356, 9,528,105, and 9,540,636; and Chinese Patent Application Publication Nos. CN 101864488 A, CN 102732504 A, CN 103667255 A, CN 104630204 A, and CN 104651350 A.

SUMMARY

Embodiments described herein provide for methods and techniques for isolating nucleic acids from samples, such as field samples. The method may include adding a chelating agent to the sample to block at least a portion of the nucleic acid binding sites on contaminants in the sample. The method may also include adding a solvent mixture, such as phenol-chloroform-isoamyl alcohol, to the sample to aid in the separation of the nucleic acids from organic contaminants in the sample. The method may further include heating the sample to aid in the removal of hydrocarbons from the sample. Additionally, the method may include using freeze-thaw cycles to lyse cells in the sample.

The methods and techniques described herein may be used to isolate and extract nucleic acids from field samples. The nucleic acids can then be sequenced or further analyzed to determine a genomic profile of the sample, and thus an identification of the area from which the sample was obtained (i.e., the sampling site). The genomic profile can then be used to aid in determining whether a hydrocarbon reservoir is located proximate to the sampling site.

DESCRIPTION OF THE FIGURES

The advantages of the present techniques are better understood by referring to the following detailed description and the attached figures, in which.

DETAILED DESCRIPTION OF THE INVENTION

In the following detailed description, specific embodiments of the techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described herein, but rather, include all alternatives, modifications, and equivalents falling within the true spirit of the invention and scope of the appended claims.

At the outset, for ease of reference, certain terms used in this application and meanings as used in the context of this application are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, and terms or techniques that serve the same or a similar purpose are considered to be within the scope of the present claims.

"Adsorption" or "adsorb" means the binding or adhesion of molecules, ions, or particles to a solid surface. The binding of a molecule to the surface of a solid is reversible when the bonds formed between the solid surface and the adsorbent are broken. A non-limiting example of adsorption as used herein includes the adhesion of nucleic acids to the surface of a metal oxide or other inorganic contaminant in a field sample.

"Amplification" is the generation of multiple copies of nucleic acid segments to enhance the analysis of very low amounts of nucleic acids. For example, amplification may be performed by a polymerase chain reaction ("PCR"), which uses a thermostable polymerase enzyme, such as the TAQ enzyme for DNA, to exponentially produce thousands or millions of copies of a DNA segment during a number of thermal cycles. During each cycle, the DNA segments produced in a previous cycle become templates for new copies of that segment. RNA analysis may be performed by reverse transcribing the RNA to create cDNA segments, which may then be amplified.

The term "field sample" refers to a sample containing material from the natural environment. Field samples include, but are not limited to, samples taken from any soil (encompassing all soil types and depths), water or liquid (encompassing freshwater aquatic or marine habitats), sediment (encompassing marine sediment, lake or river sediment, or mud sediment), or atmospheric dust or particulates. The field sample may include a multitude of species of microorganisms or a single species of microorganism.

A "geologic model" is a computer-based representation of a subsurface earth volume, such as a petroleum reservoir or a depositional basin. Geologic models may take on many different forms. Depending on the context, descriptive or static geologic models built for petroleum applications can be in the form of a 2-D or 3-D array of cells, to which geologic and/or geophysical properties such as lithology, porosity, acoustic impedance, permeability, or water saturation are assigned (such properties are referred to collectively herein as "reservoir properties"). Many geologic models are constrained by stratigraphic or structural surfaces (for example, flooding surfaces, sequence interfaces, fluid contacts, and/or faults) and boundaries (for example, facies changes). These surfaces and boundaries define regions within the model that possibly have different reservoir properties.

A "hydrocarbon" is an organic compound that primarily includes the elements hydrogen and carbon, although nitrogen, sulfur, oxygen, metals, or any number of other elements may also be present in small amounts. As used herein, hydrocarbons generally refer to organic materials (e.g., natural gas and liquid petroleum) that are harvested from hydrocarbon containing sub-surface rock layers, termed reservoirs.

"Lysing" is the disruption of membranes in a cell, such as the cell wall and/or the nuclear membrane to release the contents. Lysing of cells for nucleic acid analysis is generally performed using techniques that avoid degradation of the nucleic acid chains.

The term "microorganism" refers to any number of microscopic single celled or multi-celled organisms. Microorganisms include bacteria, archea, protozoans, fungi, and algae. The techniques described herein may be particularly useful for isolating nucleic acids from bacteria and archea microorganisms. Nucleic acids may be extracted from field samples, and then used to identify microorganisms present in the sample. Further, even in the absence of identification, the nucleic acids present may be used to create genetic signatures that may be correlated to other factors in the environment.

The term "natural gas" refers to a multi-component gas obtained from a crude oil well (associated gas) or from a subterranean gas-bearing formation (non-associated gas). The composition and pressure of natural gas can vary significantly. A typical natural gas stream contains methane as a significant component. Raw natural gas also typically contains higher carbon number compounds, such as ethane, propane, and the like, as well as acid gases (such as carbon dioxide, hydrogen sulfide, carbonyl sulfide, carbonyl disulfide, and mercaptans), and minor amounts of contaminants such as water, nitrogen, iron sulfide, wax, and crude oil.

The term "nucleic acid" refers to biopolymers used in cells for the transfer of information. Nucleic acids include deoxyribonucleic acid ("DNA"), which is generally found in a nucleus of a eukaryotic cell, and ribonucleic acid ("RNA"), which is generally found in the cytoplasm of a eukaryotic cell. A prokaryotic cell, such as a bacterial or archea cell, does not have a nucleus; however, both DNA and RNA may be found in the cytoplasm of the prokaryotic cell. DNA often provides the genetic code for a cell, although a few types of organisms use RNA to carry heritable characteristics. RNA is often associated with the synthesis of proteins from genes on the DNA.

A "reservoir" is a subsurface rock formation from which a production fluid can be produced. The rock formation may include granite, silica, carbonates, clays, and organic matter, such as oil, gas, or coal, among others. Reservoirs can vary in size from less than one cubic foot ($0.3048$ $m^3$) to hundreds of cubic feet (hundreds of cubic meters). The permeability of the reservoir rock may provide paths for production and for hydrocarbons to escape from the reservoir and move to the surface.

A "seep" or petroleum seep is a place where hydrocarbons escape to the surface, normally under low pressure or flow. Seeps may occur above either terrestrial or offshore petroleum reservoirs, but may also occur above subsurface deposits of organic material, for example, as the organic material degrades. The hydrocarbons may escape from the reservoir or deposit along geological layers, or through fractures and fissures in the rock.

"Sequencing" is the determination of the order of structural elements, or sequence, of a nucleic acid, such as DNA or RNA. Generally, the term refers to the determination of the sequence of a nucleic acid chain, which may be used to identify organisms found in an environment. These may include microorganisms, such as bacteria or archea, found near seeps.

"Substantial" when used in reference to a quantity or amount of a material, or a specific characteristic thereof, refers to an amount that is sufficient to provide an effect that the material or characteristic was intended to provide. The exact degree of deviation allowable may in some cases depend on the specific context.

Hydrocarbons from various subsurface sources may be released at the surface, or into water columns, as seeps. The presence of the hydrocarbons may be confirmed by any number of measurements, including, for example, gas chromatography, liquid chromatography, or by the presence of biological materials that are associated with hydrocarbons. The source of the hydrocarbons may be identified by the presence and type of microorganisms present at the seep, for example, in the subsurface environment, the surface environment, or in the water column.

Microorganisms within a sample may be identified by sequencing the nucleic acid chains present in the sample. A distribution of species present in a sample may then be used to locate and/or identify hydrocarbon reservoirs. For example, a preponderance of microorganisms associated with decaying organic matter may indicate that the hydrocarbons have been generated in the subsurface environment, and are not associated with a hydrocarbon reservoir. However, a preponderance of microorganisms that use hydrocarbons only as metabolic fuel may indicate the presence of a reservoir. Additionally, nucleic acid sequencing may also be used to generate ecologic "signatures" or "fingerprints" that may be associated with reservoirs in particular environments, such as mapping of genomic profiles in the absence of specific identification of microorganisms.

However, nucleic acid extraction from field samples can be problematic. Compounds found in the field, such as iron oxides, clay minerals, aqueous inorganic ions, dissolved and or liquid phase hydrocarbons, and many others, can affect the efficiency of nucleic acid isolation and extraction techniques. These materials can also affect the subsequent ability to amplify the nucleic acids and/or sequence the nucleic acids. Further, nucleic acids from certain types of organisms and/or certain sample types may be easier to extract than others.

Provided herein are techniques to extract and isolate nucleic acids, such as DNA and RNA, from field samples that may comprise hydrocarbon bearing sediment, hydrocarbon free sediment, filtered oil-water emulsions, filtered oils, and/or filtered waters. The techniques may be used to extract nucleic acids from field samples with similar efficiency across a wide variety of sample and organism types. For example, the techniques can be used on a variety of sample types containing known concentrations of nucleic acids, and yield similar concentrations of nucleic acids, e.g., in nanograms (ng) DNA per gram (g) sample, for each sample type. Thus, the techniques can remove some of the bias that may exist between different types of field samples, such as solid samples, water column samples, and the like, making the results for samples of different types more comparable.

The extraction techniques described herein may include the addition of chelators to the sample solution to passivate the surface of contaminant materials in the sample, decreasing adsorbance of nucleic acids onto these contaminants. Further, the use of freeze/thaw cycles may increase the effectiveness of lysing of cells to increase the amount of nucleic acids extracted from the sample. Further, heat cycles may be used to remove hydrocarbons from the sample, increasing the effectiveness of the extraction techniques. Further, a solvent mixture, such as a phenol/chloroform/isoamyl alcohol, may be added to aid in the phase separation of the sample.

Figure 1:
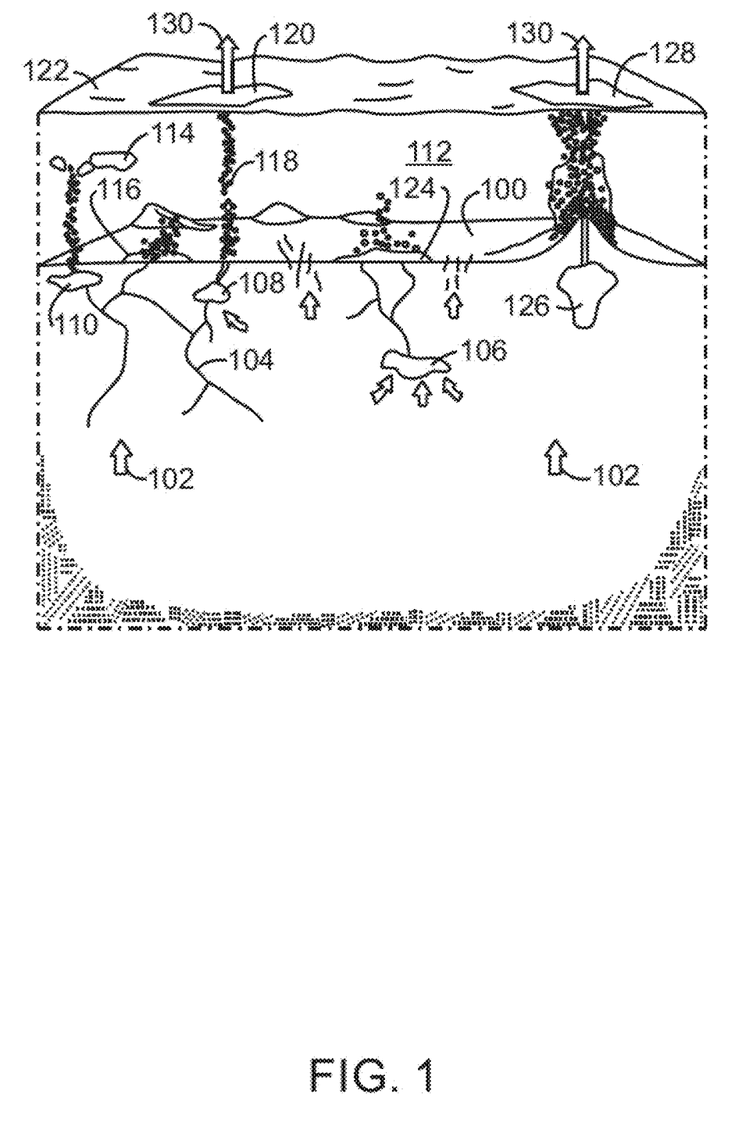
FIG. 1 is a schematic diagram illustrating numerous subsurface sources and migration pathways of hydrocarbons that may be present at or escaping from seeps on the seafloor.
Figure 2:
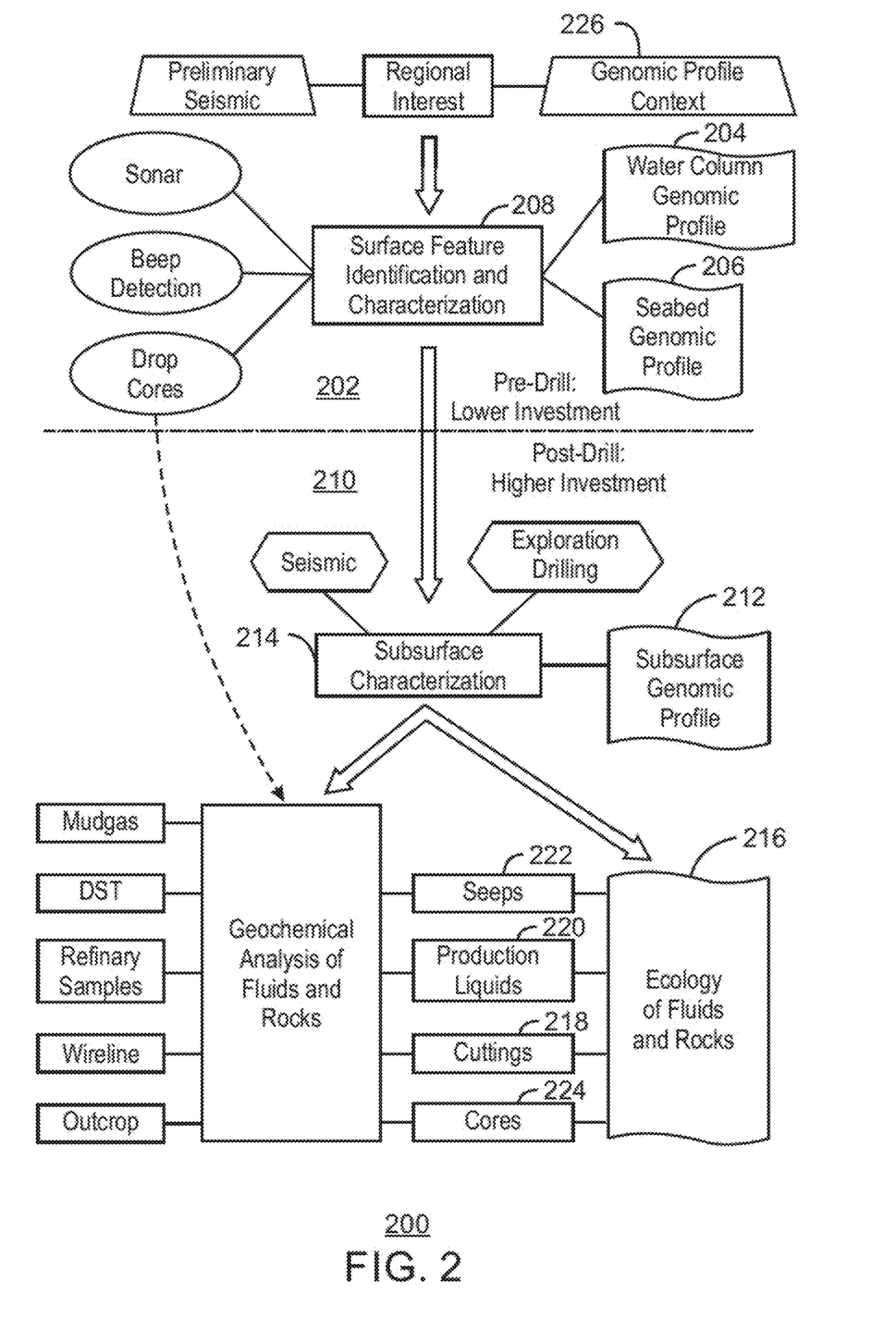
FIG. 2 depicts an exemplary workflow for oil and gas exploration illustrating instances within the workflow where ecological analysis of microorganisms, e.g., profiling the nucleic acids in a sample from a location of interest, may be performed to assess the conditions of a hydrocarbon reserve.

The techniques may be used in oil and gas exploration, for example, to map traces of nucleic acids to hydrocarbon reservoirs, as discussed further with respect to FIGS. 1 and 2. However, the techniques for extracting nucleic acids described herein are not limited to locating hydrocarbon reservoirs, but may also be used in any number of other applications. For example, the techniques may be used in environmental remediation to study microorganisms present in the vicinity of chemical or radionuclide contamination. The techniques may be used to map areas of contamination for further remediation work, such as remediating contaminated soil. Other applications may include archeological studies where the techniques are used to map the presence of genomic traces in a dig site. In archeological application, the organisms that are targeted may not solely be microorganisms, but may also include remains of plants and other organisms.

FIG. 1 is a schematic diagram illustrating numerous subsurface sources and migration pathways of hydrocarbons that may be present at or escaping from seeps on the ocean floor 100. Hydrocarbons 102 generated at source rock (not shown) migrate upward through faults and fractures 104. The migrating hydrocarbons may be trapped in reservoir rock and form a hydrocarbon accumulation, such as a gas reservoir 106, oil and gas reservoir 108, or a gas hydrate accumulation 110. Hydrocarbons seeping from the gas hydrate accumulation may dissolve into methane in the water column 112 as shown at 114, or may remain as a gas hydrate 116 on the ocean floor 100. Alternatively, oil or gas from oil/gas reservoir 108 may seep into the ocean, as shown at 118, and form an oil slick 120 on the ocean surface 122.

A microorganism colony, such as a bacterial mat 124, may form at a gas or oil seep location, for example, as gas leaks from a gas reservoir 106. As the microorganisms use the hydrocarbons for energy, they may generate biogenic hydrocarbon gases while degrading thermogenic wet gas. Still another process of hydrocarbon seepage is via a mud volcano 126, which can form an oil slick 128 on the ocean surface. Oil slicks 120 and 128 or methane gas 130 emitted therefrom are signs of hydrocarbon seepage that are, in turn, signs of possible subsurface hydrocarbon accumulation.

The ecology of a hydrocarbon system, e.g., the types of microorganisms or the more general genomic profile, present in the vicinity of a seep, may provide information useful in oil and gas exploration. For example, morphology of mineral precipitate structures (e.g., Beggiatoa mats) has been coupled with mapping seep, fault, and subsurface geology. Further, it is possible to use biological information for exploration and hydrocarbon characterization purposes. For example, certain types of microorganisms should be identifiable and be more abundant where the greatest volume of hydrocarbon has accumulated. Thus, organisms associated with degradation of non-petroleum subsurface organic matter, may be less abundant in regions where hydrocarbons are migrating from reservoirs. Whereas, organisms associated with the consumption of hydrocarbons, may be more abundant in regions where hydrocarbons are migrating from reservoirs.

However, in some examples, the species identification of specific microorganisms is not needed. That is, a genomic profile (i.e., fingerprint or signature), or DNA or RNA map, of locations in a hydrocarbon rich environment may allow correlations to be made that can identify which locations are associated with hydrocarbons from a reservoir versus hydrocarbons formed by decay of organic matter. These correlations may increase the probability that a sampling site is proximate to a hydrocarbon reservoir to be determined.

FIG. 2 depicts an example workflow 200 for oil and gas exploration illustrating places within the workflow where ecological analysis of microorganisms, e.g., profiling the nucleic acids at a location, may be performed to assess the conditions of a hydrocarbon reservoir. Referring also to FIG. 1, during pre-drill activities 202 water samples may be taken at or near a suspected seep 118 to identify 204 the microorganisms present in the water column 112. To control for microorganisms present in the water column that are not associated with a seep 118, a water sample may also be taken in a region in the water column 112 where there are no known seeps. Other samples may be taken from shallow sediment on the ocean floor, for example, near seeps 118, hydrates 116, or bacterial mats 124 to identify 206 the microorganisms present on or near the ocean floor 100. Analysis of samples from the water column 204 and the seafloor 206 yield information about surface feature identification and characterization 208. During post-drilling activities 210, identification 212 of microorganisms, such as bacteria or archea, in the subsurface may aid subsurface characterization 214. Samples taken from the reservoir fluids and the drill core may help determine the subsurface ecology 216 of fluids and rock, respectively, including, for example, the identification of any microorganisms present. The ecology 216 of fluids and rocks may also use cuttings 218, production liquids 220, seeps 222, and other core samples 224.

The collection of the data on the identity of microorganisms may provide a genomic profile context 226 that may be used for further exploration. The genomic profile context 226 may include statistical maps of microorganism associated with reservoirs and subsurface deposits of organic matter. Further, specific identification of specific microorganism species may not be necessary, as a general genomic profile may be used for mapping sites associated with subsurface reservoirs.

Previously, the collection of biological information for hydrocarbon systems used culture based techniques. However, these techniques may be limited by the ability of the organisms to be cultured. Many organisms associated with hydrocarbon deposits, particularly those that may be found within a hydrocarbon reservoir, are not able to be cultured. Further, earlier studies often assumed that the organisms living in the subsurface were similar to those at the surface. However, recent evidence indicates that the biodiversity in the subsurface is quite complex and many of the subsurface species found have not been previously identified.

Genetic divergence from known reference species may complicate probe-based methods that use genetic similarity to known organisms. However, the increasing sensitivity and lower costs of PCR techniques and high throughput sequencing can make metagenomics, tag sequencing, and other large volume sequencing techniques that can be used for large scale mapping of genetic occurrences more practical for use in exploration. To use these techniques, effective preparation techniques are needed to maximize the amount of nucleic acid obtained from samples.

Samples, such as those from soil, sediment, or a water column, may contain contaminating materials that bind to the nucleic acids in the sample. For example, the sample may contain materials, such as metal oxides ("MOXs") that may be present in rust, sediments, clays, and other materials. If the cells are lysed while the contaminants are present, the nucleic acids may bind to the contaminants rather than being eluted at later extraction stages. The effect of the contaminants may also be exacerbated in fluid samples, where the samples are typically first filtered to concentrate any microorganism that are present in the sample, which can also have the effect of concentrating the contaminating materials that bind to the nucleic acid.

In the techniques disclosed herein, a chelating agent solution may be added to passivate the surface of contaminants in the sample prior to the lysing process. That is, use of the chelating agent solution may passivate the positively charged binding sites on the contaminants that would otherwise bind to nucleic acids in the sample. Therefore, use of the chelating agent solution can block the adsorption sites and decrease adsorption of nucleic acids onto the binding sites of the contaminants. Useful chelating agent solutions that may be used include solutions of sodium phosphate, sodium oxalate, ethylenediaminetetraacetate acid, siderphores, and mixtures thereof. In preferred embodiments, the chelating agent solution is a solution of sodium phosphate or sodium oxalate.

The proportion of chelating agent needed may depend on the number of binding sites on the contaminants that may be present in the sample which can be highly variable. Accordingly, an excess of chelating agent solution may be used. For example, the amount of chelating agent may range from 1 µl to 10 ml, or greater, depending on the amount of solids in the sample. For example, the amount of chelating agent solution may be greater than 25 µl, or greater than 30 µl, or greater than 50 µl, or greater than 75 µl, or greater than 100 µl, or greater than 150 µl, or greater than 175 µl, and may be less than 10 ml, or less than 7 ml, or less than 5 ml, or less than 2 ml, or less than 1 ml, or less than 500 µl, or less than 300 µl, or less than 250 µl. For example, if a chelating agent solution having a 5.0 M concentration of sodium phosphate is used, the amount may be between 25 µl and 300 µl, or from 50 to 300 µl, or from 100 to 300 µl. In some embodiments, the amount of chelating agent solution may be about 50 µl, or about 100 µl, or about 150 µl, or about 170 µl, or about 180 µl, or about 190 µl, or about 200 µl, or about 250 µl. The amount used may be selected based on the amount of solids in the sample. In some examples described herein, about 180 µl of a 5.0 M solution of sodium phosphate is used.

As the binding sites often have a positive charge, the pH of the chelating agent solution may be controlled to enhance adsorption of the chelating agent onto the contaminants. Further, control of the pH may protect the nucleic acid from degradation. For example, the pH may be adjusted for the chelating agent solution to be greater than 7.0, or to be between 7.0 and 9.0, or between 7.0 and 8.0, or between 7.1 and 7.6, or between 7.2 and 7.4. If the chelating agent used is a sodium phosphate solution, the sodium phosphate solution may also act as a buffer in addition to being a chelating agent.

The lysing conditions used may control the amount of nucleic acid released from cells in the sample. Easy to lyse cells may not require aggressive conditions, while some types of microorganisms may require more aggressive lysing conditions. In some embodiments, lysing may be accomplished by heating the sample to lyse the cells. While in other embodiments, lysing may be accomplished through the use of freeze/thaw cycles. In further embodiments, lysing may be accomplished through the use of both heating of the sample and the use of freeze/thaw cycles.

Heat may be used in the lysing procedure to lyse the cells. For example, the sample may be heated, or placed in a heated incubator, for a time period in the range of from about 1 minute to about 10 minutes, or from about 2 minutes to about 8 minutes, or from about 3 minutes to about 7 minutes, or from about 4 minutes to about 6 minutes, or for about 5 minutes. For cells that do not require aggressive lysing conditions, the sample may be incubated for a time of less than 5 minutes, or less than 4 minutes, or less than 3 minutes, or less than 2 minutes, such as a time period between 1 minute and 5 minutes. The time period at which the sample is incubated may also be increased or decreased depending on the incubation temperature. For example, the sample may be incubated at a temperature of less than 100° C., or less than 95° C., or less than 90° C., or less than 85° C., or less than 80° C., or less than 75° C., or less than 70° C., or less than 65° C., or less than 60° C. For example, the sample may be incubated at a temperature in the range greater than 40° C., or greater than 45° C., or greater than 50° C., or greater than 55° C. For example, the sample may be incubated at a temperature of from 50° C. to 100° C., or from 55° C. to 95° C., or from 50° C. to 75° C., or from 60° C. to 80° C., or from 55° C. to 85° C. For samples that are being processed for RNA extraction, lower temperatures or shorter times may be used to avoid degradation of the RNA, while samples that are being processed for DNA extraction may be incubated at higher temperatures or for longer times.

While incubating the sample may assist in the lysing of the cells within the sample, the high temperature lysing may fail to disrupt a sufficient number of cells to provide a substantial nucleic acid sample. Additionally, for some samples, high temperature lysing may be too aggressive and lead to degradation of the nucleic acid released. Furthermore, lysing may release the nucleic acid too early, e.g., before steps that remove hydrocarbon contamination from the sample. Thus, in some embodiments, freeze-thaw cycles can be used to lyse the cells in the sample, as an alternative to or in addition to the high temperature lysing.

For freeze-thaw cycle lysing, the sample may be frozen using, for example, immersion in liquid nitrogen, dry ice or acetone, or other cryogenic cooling fluids in a dewar or other freezing apparatus such as a cryogenic freezer. After freezing, the sample is removed and thawed. If freezing materials other than liquid nitrogen are used, the sample container may be placed inside another container to prevent exposure to the freezing material, such as the acetone or other solvent. The thawing may be performed at a temperature of between about 20° C. and about 60° C., or between about 20° C. and about 30° C., or at a temperature of about 22° C., or about 30° C., or about 40° C., or about 50° C., or higher. If an elevated temperature is used, the thawing time is generally kept short to avoid degradation of the nucleic acids. For example, the sample may be exposed to the elevated thawing temperature for a time between about 30 seconds and 4 minutes, or a time about 3 minutes, or about 2 minutes, or about 1 minute or less. Shorter times may be used for RNA isolation than for DNA isolation.

A number of freeze/thaw cycles may be used to perform the lysing. For example, 5 cycles, or 4 cycles, or 3 cycles, or 2 cycles, or 1 cycle may be used depending on the types of organisms that are expected to be present in the sample. For example, in some embodiments, the lysing is performed by three freeze-thaw cycles using liquid nitrogen as the freezing agent.

After lysing, the lysed material, termed the "lysate", may be removed from the sample into an apparatus for further treatment or lysing. For example, depending on the isolation protocol, the lysing apparatus may be a bead tube or similar apparatus.

A solvent may be added to the sample to enhance the separation of the nucleic acids of interest from other materials that may be present in the sample. For example, a solvent may be used to enhance separation of DNA from the RNA, proteins, and hydrocarbons present in the sample. The solvent used may be a mixture of phenol, chloroform, and isoamyl alcohol used in a ratio where the phenol is present from about 20 volume % ("vol %") to 30 vol %, or from 22 vol % to 28 vol %, or from 23 vol % to 27 vol %, or from 24 vol % to 26 vol %, the chloroform is present from about 20 vol % to 30 vol %, or from 21 vol % to 27 vol %, or from 22 vol % to 26 vol %, or from 23 vol % to 25 vol %, and the isoamyl alcohol is present from about 0.5 vol % to about 5 vol %, or from 0.75 vol % to 3 vol %, or from 0.8 vol % to 2 vol %, where the total amount of phenol, chloroform, and isoamyl alcohol add up to 100 vol %. For example, in some embodiments, the solvent is a phenol-chloroform-isoamyl alcohol ("PCI") mixture used at a ratio of about 25:24:1. The pH of the solvent may be adjusted depending on the type of nucleic acids being isolated. For example, if the solution is acidic, RNA may be retained in the aqueous phase of the sample, while if a higher pH is used, DNA may be retained in the aqueous phase of the sample. Thus, is RNA is the target nucleic acid for extraction, the pH of the solvent may be less than 7, while if DNA is the target nucleic acid for extraction, the pH of the solvent may be greater than 7.

The amount of solvent that may be used depends on the amount of the other materials expected to be present in the sample. For example, the amount of solvent used may be between about 25 µl to about 150 µl, or from about 50 µl to about 150 µl, or from 75 µl to about 125 µl. In some embodiments, the amount of solvent used may be greater than about 50 µm, or greater than about 75 µl, or greater than about 100 µl, or greater than about 125 µl. In some embodiments, about 100 µl of PCI may be added to the lysate.

The presence of hydrocarbons in the field sample may lead to degradation of the nucleic acids, or to interference in the analysis of the nucleic acids. Accordingly, the sample may be heated to remove the hydrocarbon. This may be performed, for example, prior to the lysing procedure to avoid damaging any released nucleic acids. For example, the solution may be heated to a temperature greater than about 40° C., or greater than about 50° C., or greater than about 60° C. For example, the solution may be heated to a temperature between about 40° C. and about 80° C., or from 50° C. to 75° C., or from 60° C. to 70° C. The heating may be done for a time between about 10 section to about 120 seconds, or for about 15 sections, or about 30 seconds, or about 60 seconds, or more. However, the time may be kept short to prevent degradation of the released nucleic acids.

Further, the hydrocarbon removal may be performed by holding the solution under a slight vacuum during heating, e.g., at a pressure differential of between about 0.2 atmospheres ("atm") and 0.95 atm, or at a pressure of about 0.25 atm, or about 0.5 atm, or about 0.75 atm, or about 0.9 atm. By reducing the pressure, the temperature needed to remove the hydrocarbons from the sample may be reduced.

After lysing, the sample may have phase separated into two or three phases, depending upon the materials present. For example, a top phase may include hydrocarbons if they are present in the sample. A middle phase may include proteins or other organic contaminants. The proteins may be entrained in a PCI layer if PCI was used as a solvent. The bottom layer may include the separated nucleic acids in an aqueous solution, which can then be collected and prepared for analysis and sequencing.

The techniques described above may be used to enhance a number of nucleic acid isolation protocols, systems, or techniques. As described below, the techniques described herein were tested as a modification to the PowerWater® Steverix™ DNA isolation protocol available as a DNA isolation kit from Mo-Bio Laboratories of Carlsbad, Calif. The kit uses Steverix™ filter units available from Merck Millipore Co. of Billerica, Mass.

EXAMPLES

The following examples illustrate the use of the techniques described herein as modifications to the PowerWater® Steverix™ DNA isolation protocol. However, as noted above the techniques may be used to enhance other DNA isolation kits as well. Further, it should be noted that the techniques described herein are not limited to modification of DNA isolation kits, as the techniques can be used with any number of different sample preparation techniques and with different sample types. For example, the techniques may be used on solid samples that are crushed prior to treatment with the chelating agent, then lysing with liquid nitrogen freeze-thaw cycles, followed by a heating cycle to remove hydrocarbons. In such an example, the supernatant fluid may be directly imposed on the DNA binding (adsorption) column after the techniques are finished.

Further, while the techniques are described in the example as being used on materials isolated with a Sterivex™ filter, the techniques may be used with other materials. For example, if the sample is a sediment or soil sample, the protocol could be started with a 2 mL bead tube having a screw cap with an O ring, or other sample tube that can withstand 5 minutes in a vortex or other centrifuge. If the sample is a sediment sample, 0.5 grams of sediment or less can be added to the tube.

The PowerWater® Steverix™ DNA isolation kit uses a multistep protocol that may be followed to isolate and concentrate DNA in a sample for further analysis by sequencing. To prepare for the tests, the solution identified as ST1A in the kit is added to a solution identified as ST1B. The resulting solution is mixed and stored at 4° C. when not in use. Solutions identified as ST2 and ST4 are warmed prior to use at 65° C. for 5 to 10 minutes in a water bath. The solutions ST2 and ST4 are used while still warm.

The procedure using the protocol from the kit as well as the enhancements described herein that were used in the examples is presented in the numbered paragraphs below.

1. Filter a liquid field sample through a Strerivex™ filter unit, available from Merck Millipore as catalog number SVGPL10RC. After filtering, a syringe containing air is used to remove as much of the remaining liquid as possible. The ends of the filter are then caped with Inlet and Outlet Caps. Typical volumes that are filtered are from 1 to 10 liters, depending on the microbial load and turbidity of the field sample. For long term storage after filtering, the Sterivex™ filter units may be stored capped and without excess liquid at −20° C. For use of a pre-filtered sample, thaw the Sterivex™ filter unit, and if there is fluid in the cartridge, push it out with a syringe once the fluid is melted.
2. Remove the Inlet Cap and add 0.8 mL of Solution ST1B using a pipette tip. Insert the pipette completely into the inlet so that the pipette tip is visible inside the unit just above the membrane.
3. Add 180 μL of 10× (i.e., 5.0 M) sodium phosphate solution having a pH of about 7.2-7.4 to the filter unit. Splashing and sample spillage should be avoided as the pipette tip is removed.
4. Re-cap the filter unit and secure the filter unit horizontally, with the inlet facing out, to a MO BIO Vortex Adaptor, catalog #13000-VI-15 or 13000-VI-5.
5. Vortex at minimum speed for 5 minutes. During the vortex, solution ST2 is immersed into a water bath to warm up as described above.
6. While still attached to the vortex adaptor, rotate the sample filter unit 180 degrees from the original position. Vortex at the minimum speed for 5 minutes.
7. Remove the filter unit from the vortex and set with the inlet facing up. Remove the Inlet Cap.
8. Add 0.8 mL of solution ST2 to the filter unit using a pipette and re-cap the inlet. When adding the ST2 solution, insert the pipette completely into the inlet such that the pipette tip is visible just inside the unit just above the membrane. When adding the ST2 solution, care should be taken to make sure that the ST2 solution is fully warmed, such that the precipitates in the solution are dissolved.
9. Heated Lysing: Heat the filter unit at 90° C. for 5 minutes in an oven. However, for samples containing easy to lyse organisms or where less shearing of the nucleic acids is desired, this step and Step 10 can be omitted. Further, if the freeze-thaw cycles are being used for lysing, this step and Step 10 may also be omitted.
10. Cool the filter unit at room temperature for 2 minutes.
11. Secure the filter unit horizontally with the inlet facing out to the vortex adaptor, and vortex at maximum speed for 5 minutes.
12. Set the filter unit on a flat surface with the inlet facing up, and remove the Inlet Cap
13. Pull back the plunger on a 3 mL syringe to fill the barrel of the syringe with 1 mL of air. Attach the syringe to the inlet of the filter unit. Hold the syringe and filter unit vertically with the syringe at the bottom to allow as much of the lysate as possible to be near the inlet.
14. Push (but do not force) air into the filter unit from the syringe until there is resistance, and release the plunger. Back pressure acts to withdraw the lysate from the filter unit and fill the syringe. Continue to pull back on the plunger to remove as much of the lysate as possible from the filter unit. Detach the syringe from the filter unit.
15. Add the lysate to a 5 mL PowerWater™ Sterivex™ glass bead tube. For sediment samples, spin the initial bead tube at max speed for 5 minutes, and pipette the supernatant into the 5 mL bead tube.

16. Freeze-Thaw Lysing: Additional lysing was performed by three freeze-thaw cycles using nitrogen as the freezing material. However, for samples containing easy to lyse organisms or where less DNA shearing is desired, this step can be omitted.
17. Add 100 μL of phenol-chloroform-isoamyl alcohol (25:24:1, pH 8) to the bead tube to improve separation of the DNA from proteins, RNA, and other organics in the sample.
18. Secure the bead tube horizontally to the vortex adaptor, and vortex at maximum speed for 5 minutes.
19. Centrifuge the tube at 4,000×g for 1 minute at room temperature.
20. Transfer the supernatant to a clean 2.2. ml collection tube. Place a pipette tip down into the beads in the bead tube and against the bottom of the tube to avoid removing unwanted phases. About 1.5 mL of supernatant may be expected to be recovered. As described herein, the PCI will form a layer that may be in the bead bed and, thus, not visible. However, the PCI layer should be avoided when extracting the DNA layer from the bead tube. Additionally, hydrocarbon rich samples may have oil in or on top of the beads, and extracting the oil with the pipette should be avoided if possible.
21. Add 300 μL of solution ST3 to the collection tube, and vortex briefly to mix the solution with the supernatant. Incubate the collection tube at 4° C. for 5 minutes. While the collection tube is incubating, place solution ST4 in a water bath as described above to warm.
22. Centrifuge the collection tube at 13,000×g for 1 minute to form a pellet from any solids in the tube.
23. Avoiding the pellet, transfer the supernatant to a clean 5 mL collection tube.
24. Remove the plunger from a 20 mL syringe, and place the syringe firmly into a binding column.
25. Attach the syringe/binding column unit to a Luer-Lok™ stopcock on a PowerVac™ manifold available from MO BIO as Catalog #11991.
26. Add 3 mL of solution ST4 to the 5 mL collection tube containing the supernatant, and vortex to mix. Care should be taken to be sure that solution ST4 is warmed, and that all of the precipitates are dissolved prior to adding it to the collection tube in order to avoid potentially clogging the binding column.
27. Load the entire 4.5 mL of supernatant into the syringe attached to the binding column.
28. Turn on a vacuum source, and open the stopcock of the port. Allow the lysate to pass through the binding column, where the passage should take about 5 to 10 minutes. For especially hydrocarbon rich samples, or samples where a large amount of oil was pipetted out of the bead tube, the column membrane may appear discolored.
29. After the lysate passed through the column completely, close the one-way Luer-Lok™ stopcock of the port. Close the ports to the samples that completed filtering to increase the vacuum pressure to the other columns.
30. While keeping the binding column attached to the Luer-Lok™ stopcock, remove the 20 mL syringe from the binding column.
31. Add 0.8 mL of solution ST5 to the binding column.
32. Shake solution ST6 to mix, and add 0.8 mL of solution ST6 to the binding column by opening the Luer-Lok™ stopcock and applying a vacuum until the solution ST6 passes through the binding column completely. Continue the vacuum for another minute to dry the membrane, and then close the port.
33. Add 0.8 mL of solution ST5 to the binding column by opening the Luer-Lok™ stopcock and applying a vacuum until the solution ST5 passes through the binding column completely. Continue the vacuum for another minute to dry the membrane, and then close the port.
34. Turn off the vacuum source, and open an unused port to the binding column to vent the manifold. However, if all ports in the binding column are in use, the vacuum can be broken at the source.
35. Once the vacuum pressure has been released, remove the binding column and placed in a 2.2 mL collection tube. Pull forward the lid of the collection tube to completely fit the cap over the binding column. Centrifuge the collection tube at 13,000×g for 2 minutes to dry the membrane.
36. Transfer the binding column to anew 2.2. mL collection tube, and add 80 μL of solution ST7 to the center of the white filter membrane. Pull forward the lid of the collection tube to completely fit the cap over the binding column. Alternatively, sterile DNA-free PCR grade water (available from MO BIO as Catalog #17000-10) can be used for elution from the silica binding column membrane at this step.
37. Centrifuge the collection tube at room temperature for 1 minute at 13,000×g.
38. The DNA in the tube is ready for analysis. If the DNA is not being processed right away, it may be frozen for storage, for example, at a temperature of about −20° C. to about −80° C.

The protocol described above was used to determine the sensitivity of the techniques with a number of different samples, such as sample size, amount of oil contamination, and the presence of salt. Additionally, the protocol was tested by varying the amount of chelator agent solution used.

Figure 3:
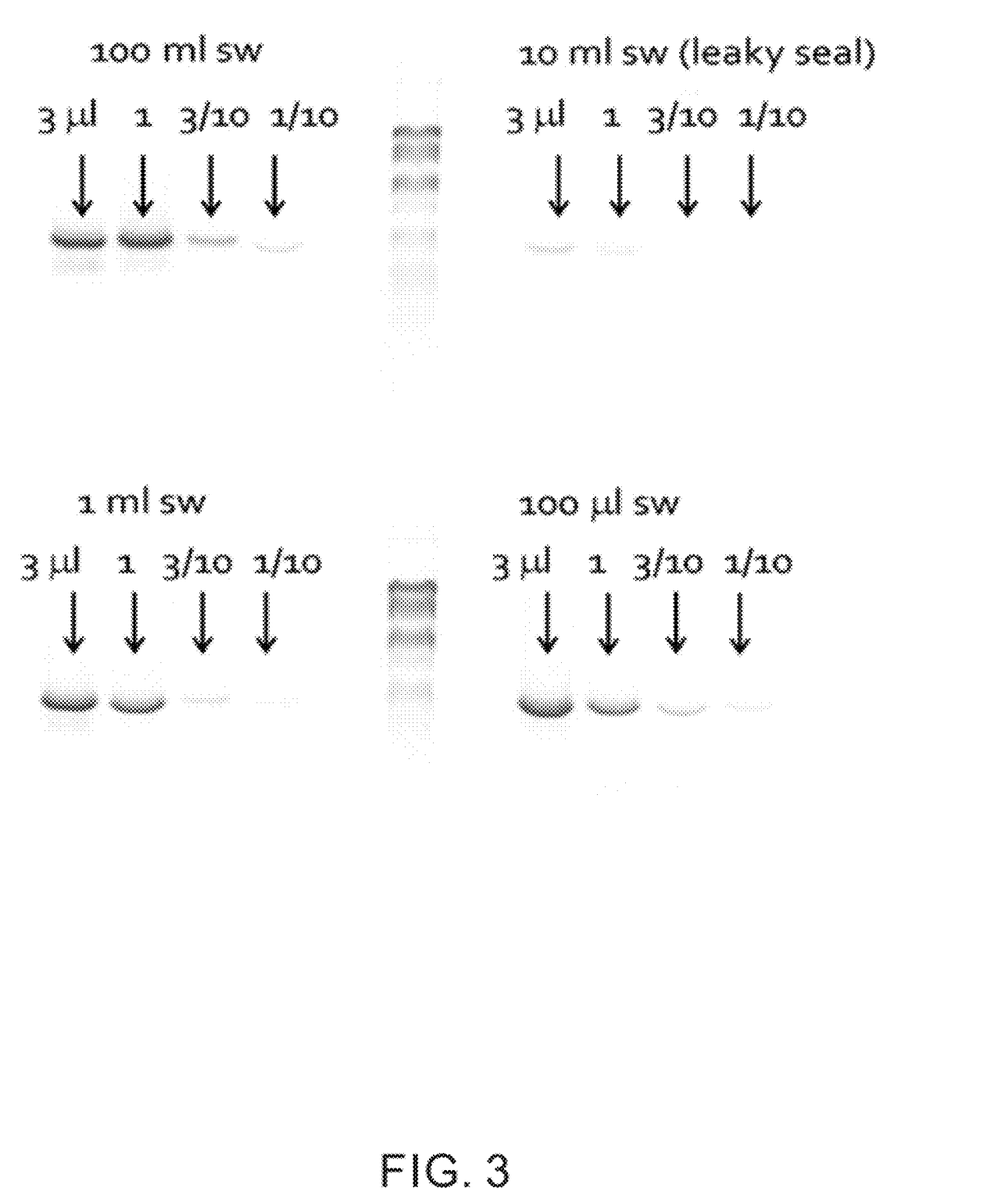
FIG. 3 is a gel electrophoresis of DNA sequencing results for a single seawater sample tested at four volumes, 100 mL, 10 mL, 1 mL, and 100 µL.

FIG. 3 is a gel electrophoresis plot of DNA sequencing results for a single seawater sample tested at four volumes: 100 mL, 10 mL, 1 mL, and 100 μL. As seen in FIG. 3, the 10 mL sample exhibited a lower signal; however, this is believed to be due to a leaky seal. Nevertheless, the sequence of the other analysis traces in FIG. 3 show that the techniques used herein do not show a significant loss of signal intensity across four orders of sample size. Thus, the techniques described herein can be used for samples of both large and small size.

Figure 4:
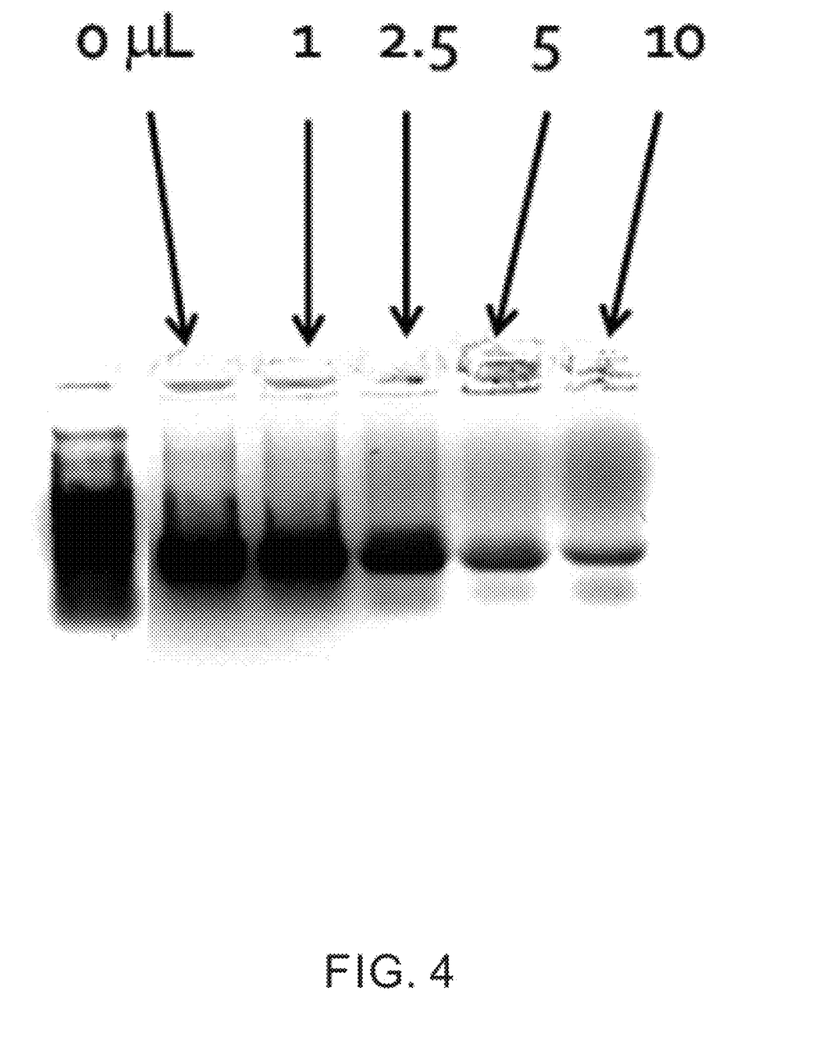
FIG. 4 is a gel electrophoresis of DNA sequencing from a series of 20 μL samples, illustrating the effects of oil addition at 0.1 μL, 2.5 μL, 5 μL, and 10 μL.

FIG. 4 is a gel electrophoresis plot of DNA sequencing from a series of 20 μL PCR samples, showing the effects of oil addition at 0, 1 μL, 2.5 μL, 5 μL, and 10 μL. Thus, in this example, the differing amounts of crude oil were added to seawater samples. Nevertheless, as seen in FIG. 4, when using the techniques described herein the addition of crude oil to the sample had only minimal effects on the extraction and sequencing of the DNA in the sample. For example, as seen in FIG. 4, substantial effects due to the crude oil were not seen until the sample contained about 25% or about 50% of oil. Thus, the techniques described herein can be used to extract nucleic acids from hydrocarbon contaminated samples.

Figure 5:
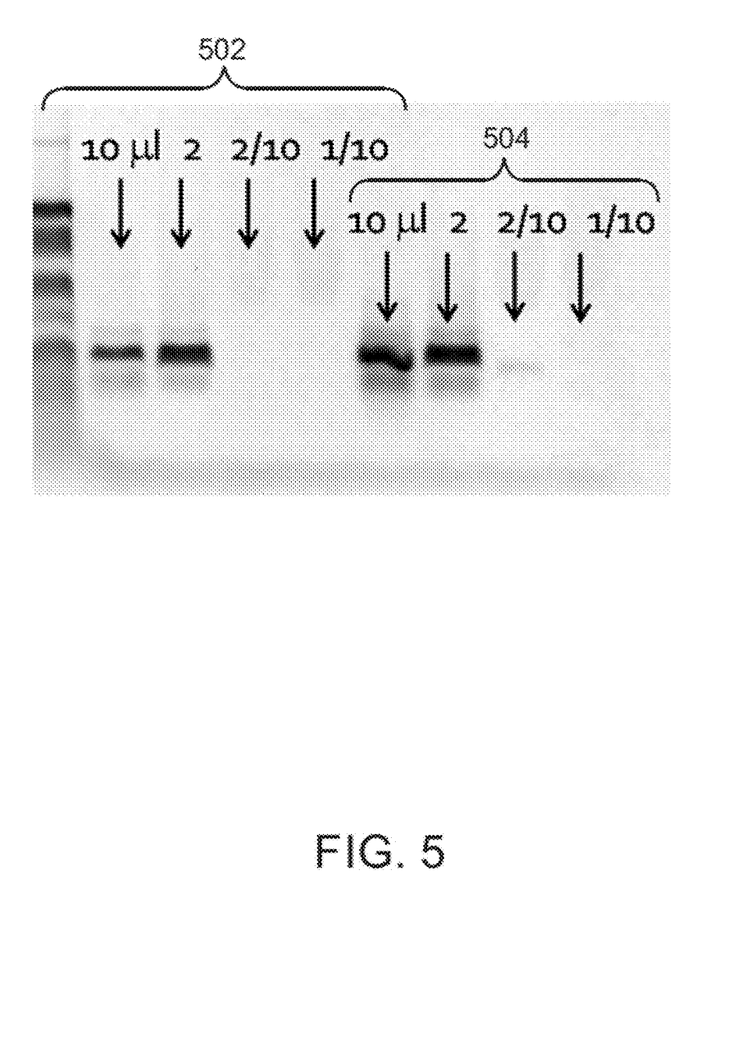
FIG. 5 is a gel electrophoresis of DNA sequencing from a 50 μL seawater samples, illustrating the effects of adding a chelating agent, such as sodium phosphate or sodium oxalate.

FIG. 5 is a gel electrophoresis plot of a DNA analysis from 50 mL seawater samples illustrating the effects of adding chelator solution, such as a sodium phosphate solution at item 502 or a sodium oxalate solution at item 504. As seen in FIG. 5, the signal intensity was higher with the addition of greater amounts of the chelator solution. Thus, the techniques described herein can be used to extract nucleic acids from samples that contain metal oxides and other contaminants that are known to adsorb DNA.

Figure 6:
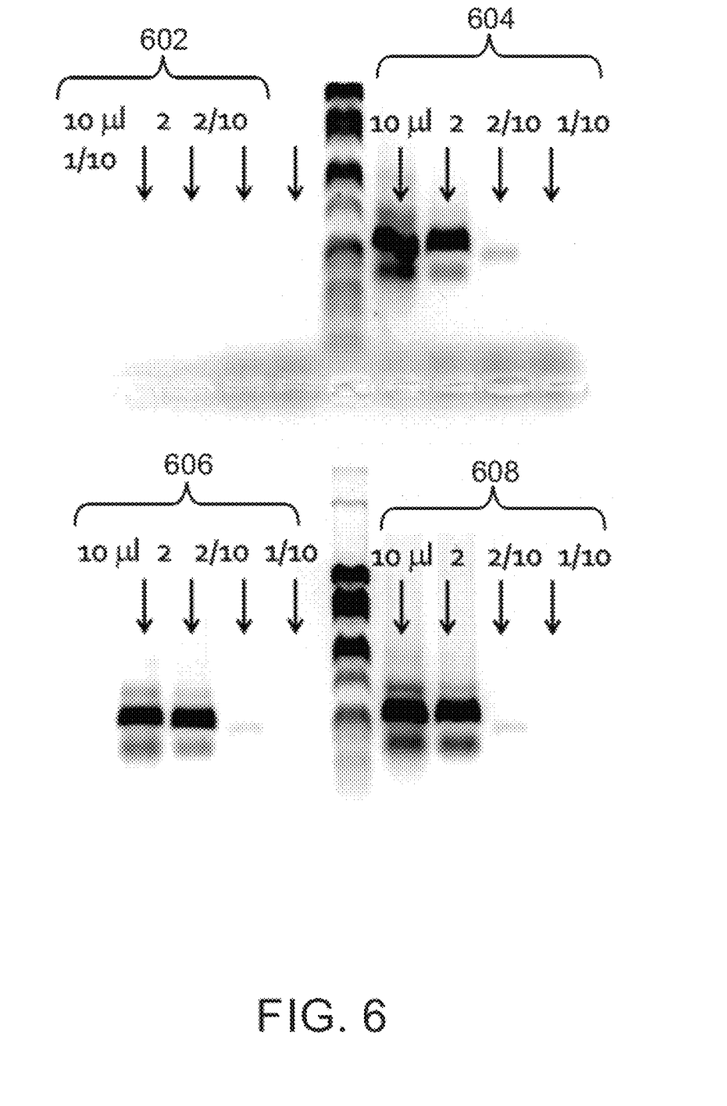
FIG. 6 is a gel electrophoresis of DNA sequencing of a series of 50 μL seawater samples, illustrating the effects of salt addition.

FIG. 6 is a gel electrophoresis plot of a DNA analysis of a series of 50 mL seawater samples, showing the effects of salt addition. The first set 602 of samples were control samples. The second set 604 of samples show the effects of adding differing amounts of a 1% sodium chloride wash to the seawater. The third set 606 of samples shown the effects of adding differing amounts of a 10% sodium chloride wash to the seawater. The fourth set 608 of samples show the effects of adding differing amounts of a 30% sodium chloride wash. As seen in FIG. 6, the yield of DNA from the samples was only minimally effected by the addition of the salt to the seawater sample. Thus, the techniques described herein can be used to extract nucleic acids from high salinity samples.

What is claimed is:

1. A method for extracting nucleic acids from cells in a field sample, comprising:
   (i) obtaining a field sample comprising hydrocarbons and cells;
   (ii) adding a chelating agent to the sample, wherein the chelating agent acts to block at least a portion of the binding sites on contaminants within the sample and wherein the chelating agent comprises a solution of sodium phosphate or sodium oxalate;
   (iii) heating the sample, wherein heating the sample acts to remove at least a portion of hydrocarbons from the sample;
   (iv) lysing the cells within the chelated sample, wherein the lysing comprises freezing and thawing the sample to lyse at least a portion of cells within the chelated sample;
   (v) adding a solvent to the lysed sample, wherein the solvent acts to separate at least a portion of the nucleic acids in the lysed samples from organic contaminants in the lysed sample and wherein the solvent comprises a mixture of phenol, chloroform, and isoamyl alcohol; and
   (vi) isolating the nucleic acids.

2. The method of claim 1, further comprising passing the sample through a filter.

3. The method of claim 1, further comprising concentrating materials from the sample through centrifugation, precipitations, or both.

4. The method of claim 1, wherein the sample is a solid sample.

5. The method of claim 1, wherein the chelating agent comprises sodium phosphate.

6. The method of claim 5, wherein greater than about 150 microliters (μl) of an about 5.0 molar solution of sodium phosphate is added to the sample.

7. The method of claim 5, wherein the chelating agent comprises a solution of sodium phosphate that has a pH of between about 7.2 and 7.4.

8. The method of claim 1, wherein the chelating agent comprises sodium oxalate.

9. The method of claim 1, wherein cells from the sample are trapped on a filter, and the method further comprises heating the filter to further lyse the cells.

10. The method of claim 9, further comprising extracting material trapped on the filter into a lysing apparatus.

11. The method of claim 10, wherein the lysing apparatus comprises a bead tube.

12. The method of claim 1, wherein lysing the cells comprises lysing the cells in a lysing apparatus by subjecting the sample to at least three freeze-thaw cycles.

13. The method of claim 12, wherein said freezing is accomplished by immersing the lysing apparatus in liquid nitrogen.

14. The method of claim 1, wherein the solvent comprises phenyl-chloroform-isoamyl alcohol (PCI).

15. The method of claim 14, wherein greater than about 75 μl of the PCI is added to the lysed sample.

16. The method of claim 1, wherein the sample is obtained from a water column above a hydrocarbon seep.

17. The method of claim 1, further comprising determining a probability that a hydrocarbon reservoir is located proximate to a sampling site by determining a genomic profile from the nucleic acids of the sample taken from the sampling site.

18. The method of claim 1, further comprising determining a probability that a hydrocarbon reservoir is located proximate to a sampling site by identifying bacteria from the nucleic acids in the sample taken from the sampling site.

19. A method for exploring an environment for a hydrocarbon reservoir, comprising:
   collecting a plurality of samples from locations in the environment, wherein the samples comprise hydrocarbons;
   extracting nucleic acids from each of the plurality of samples using a nucleic acid isolation kit comprising:
      adding a chelating agent to the sample to passivate at least a portion of the surface of contaminants in the sample that bind to nucleic acids, wherein the chelating agent comprises a solution of sodium phosphate or sodium oxalate;
      heating the sample to remove at least a portion of the hydrocarbons in the sample;
      lysing the cells in the chelated sample to release the nucleic acids; and
      adding a solvent to the chelated sample to separate at least a portion of the nucleic acids in the sample from organic contaminants in the lysed sample, wherein the solvent comprises a mixture of phyol, chloroform, and isoamyl alcohol;
   amplifying the extracted nucleic acids by polymerase chain reaction to form a nucleic acid trace;
   analyzing the nucleic acid trace to generate a genetic profile of the environment; and
   correlating the genetic profile to the presence of hydrocarbons from a reservoir.

20. The method of claim 19, wherein the chelating agent comprises sodium phosphate.

21. The method of claim 19, wherein the chelating agent comprises sodium oxalate.

22. The method of claim 19, wherein lysing the cells comprises at least three freeze-thaw cycles.

23. The method of claim 19, further comprising heating the sample to remove hydrocarbons.

24. The method of claim 23, wherein the sample is heated under a partial vacuum.

25. The method of claim 19, further comprising creating a genomic map of the locations in the environment from which the plurality of samples were obtained.

* * * * *